United States Patent
Cathey, Jr. et al.

(10) Patent No.: US 9,329,407 B2
(45) Date of Patent: May 3, 2016

(54) EXTENDED DEPTH FIELD OPTICS WITH VARIABLE PUPIL DIAMETER

(75) Inventors: W. Thomas Cathey, Jr., Boulder, CO (US); Robert H. Cormack, Erie, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 358 days.

(21) Appl. No.: 13/822,635

(22) PCT Filed: Sep. 13, 2011

(86) PCT No.: PCT/US2011/051438
§ 371 (c)(1),
(2), (4) Date: Aug. 5, 2013

(87) PCT Pub. No.: WO2012/037154
PCT Pub. Date: Mar. 22, 2012

(65) Prior Publication Data
US 2013/0308186 A1    Nov. 21, 2013

Related U.S. Application Data

(60) Provisional application No. 61/382,090, filed on Sep. 13, 2010.

(51) Int. Cl.
*G02C 7/04* (2006.01)
*G02B 27/00* (2006.01)
(Continued)

(52) U.S. Cl.
CPC ............ *G02C 7/04* (2013.01); *G02B 27/0025* (2013.01); *G02B 27/0075* (2013.01); *G02C 7/022* (2013.01); *G02C 7/042* (2013.01);
(Continued)

(58) Field of Classification Search
CPC ............ G02B 2/00; G02B 23/00; G02B 5/08; G02B 21/00; G02B 25/00; G02B 3/00; G02B 21/02; G02C 7/00; G02C 7/044; G02C 7/046; G02C 7/042
USPC .......... 359/404, 407, 656; 351/159.38, 159.3, 351/160 H, 161, 162, 159.02, 159.01, 159.1, 351/159.14, 159.74; 623/6.11, 6.17; 356/124.5
See application file for complete search history.

(56) References Cited

U.S. PATENT DOCUMENTS 4,580,882 A   4/1986  Nuchman et al.
5,225,858 A   7/1993  Portney
(Continued)

OTHER PUBLICATIONS

Zalevsky et al., This spectacles for myopia, presbyopia and astigmatism insensitive vision, Optics Express, Aug. 20, 2007, vol. 15, No. 17, pp. 10790-10803.
(Continued)

*Primary Examiner* — Darryl J Collins
*Assistant Examiner* — Journey Sumlar
(74) *Attorney, Agent, or Firm* — Jennifer L. Bales; Macheledt Bales LLP

(57) ABSTRACT

Apparatus and methods to increase the depth of field in human vision in order to correct for loss in refocusing ability. Optics variations, such as changes in thickness, shape, or index of refraction of contact lenses, intraocular implants, or the shape of the cornea or eye lens, affect the phase, or wavefront, of the light perceived by the eye. The optics variations are chosen such that the resulting optical transfer function remains relatively constant over a desired range of object distances and pupil diameters.

11 Claims, 12 Drawing Sheets

(51) Int. Cl.
*G02C 7/02* (2006.01)
*A61F 2/14* (2006.01)
*G02B 21/02* (2006.01)
*G02B 23/00* (2006.01)

(52) U.S. Cl.
CPC *A61F 2/14* (2013.01); *G02B 21/02* (2013.01); *G02B 23/00* (2013.01)

(56) References Cited

U.S. PATENT DOCUMENTS

| | | | |
|---|---|---|---|
| 5,260,727 A | | 11/1993 | Oksman et al. |
| 5,684,560 A | | 11/1997 | Roffman et al. |
| 5,715,031 A | | 2/1998 | Roffman et al. |
| 5,748,371 A | * | 5/1998 | Cathey et al. ............. 359/558 |
| 5,757,458 A | | 5/1998 | Miller et al. |
| 5,905,561 A | | 5/1999 | Lee et al. |
| 5,965,330 A | | 10/1999 | Evans et al. |
| 6,536,898 B1 | | 3/2003 | Cathey, Jr. |
| 6,540,353 B1 | | 4/2003 | Dunn |
| 6,544,424 B1 | | 4/2003 | Miller et al. |
| 6,808,262 B2 | | 10/2004 | Chapoy et al. |
| 7,025,454 B2 | | 4/2006 | Cathey, Jr. |
| 7,061,693 B2 | | 6/2006 | Zalevsky |
| 7,158,317 B2 | | 1/2007 | Ben-Eliezer et al. |
| 7,218,448 B1 | | 5/2007 | Cathey, Jr. et al. |
| 7,436,595 B2 | | 10/2008 | Cathey, Jr. et al. |
| 7,583,442 B2 | | 9/2009 | Cathey, Jr. et al. |
| 2011/0026909 A1 | * | 2/2011 | Liege et al. ............. 396/63 |
| 2012/0290085 A1 | | 11/2012 | Hong et al. |

OTHER PUBLICATIONS

Ojeda-Casteneda et al., High focal depth by apodization and digital restoration, Applied Optics, Jun. 15, 1988, vol. 27, No. 12, pp. 2583-2586.
Ben-Eliezer et al., Experimental realization of an imaging system with an extended depth of field, Applied Optics, May 10, 2005, vol. 44, No. 14, pp. 2792-2798.
Zlotnik et al., Extended depth of focus contact lenses for presbyopia, Optics Letters, Jul. 15, 2009, pp. 2219-2221.
Mino et al., Improvement in the OTF of a Defocused Optical System Through the Use of Shaded Apertures, Applied Optics, Oct. 1971, vol. 10, No. 10, pp. 2219-2225.
Dowski et al., Applied Optics, Apr. 10, 1995, vol. 34, No. 11, pp. 1859-1866.
Ojeda-Casteneda et al., Applied Optics, Mar. 1, 1990, vol. 29, No. 7, pp. 994-997.

* cited by examiner

In and Out of-Focus MTFs:
Normal Eye and EDOF Contact lens

In Focus

Out of Focus (1 Diopter)

Zeros in MTF

Normal Eye

EDOF Contact lens

CooperVision Frequency® 55 Center-distance Performance

CooperVision Frequency® 55 Center-near Performance

Acuvue Bifocal +1.0D

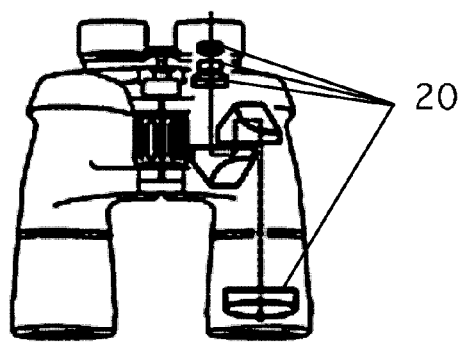
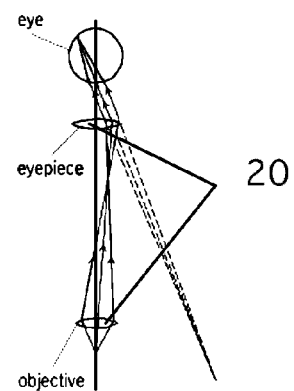
Figure 9A                               Figure 9B
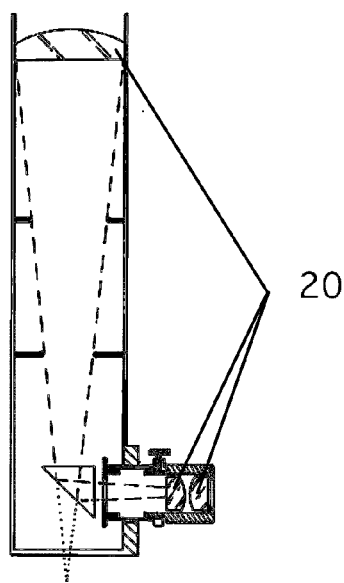
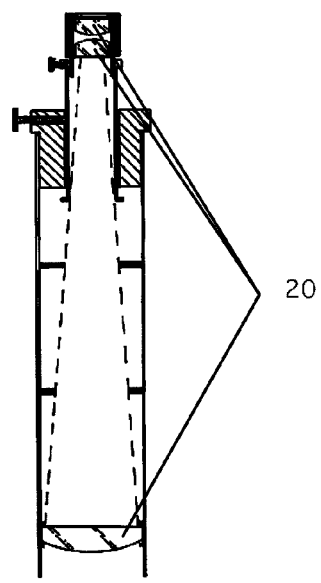
Figure 9C                               Figure 9D

EXTENDED DEPTH FIELD OPTICS WITH VARIABLE PUPIL DIAMETER

BACKGROUND OF THE INVENTION

1. Field of the Invention

The present invention relates to extending depth of field in human vision by causing the response to be largely independent of both distance to an object and pupil diameter. In particular, the present invention causes the optical transfer function of an optical element to remain relatively constant over a range of pupil diameters and distances.

2. Description of the Related Art

In the human eye, it is well known that the accommodation of the lens (or refocusing ability) decreases with age, resulting in an inability to focus over the usual range of distances. In addition, individuals with wrinkled retina have poor or no vision in a portion of the field of view. FIG. 1A (Prior Art) shows a human eye 10 with cornea 26, pupil 27, lens 28, vitreous humor 29, and retina 30 having a retina wrinkle or macular pucker 31.

Myopia, nearsightedness, is when light 41 from a distant object produces a focus in front of the retina 30 and hence a misfocus 70 at the retina, as shown in FIG. 1B (Prior Art). The eyeball is too long. Hyperopia, farsightedness, is when the light from a distant object does not focus on the retina; it would focus behind the retina, if it could pass through. The eyeball is too short. Then, there is presbyopia, which is when the lens hardens with age, and makes it difficult to focus up close. Presbyopia is an age-related farsightedness.

Various devices and techniques have been developed to partially remedy these changes in refocusing ability. Bifocal or trifocal glasses lenses provide the ability for the user to apply different prescriptions at different objects ranges by looking though selected areas of the lenses. When an eye lens must be replaced, an intraocular implant is usually designed for viewing objects at infinity, and the person then uses reading glasses and other glasses of various strengths for vision at closer distances. Other techniques include contact lenses providing two or more foci, one each for reading and for distance vision, for example. Some lenses have several rings of alternating long and short focus. This is done either with a shorter focal length lens placed in the center of a lens of longer focal length, for example, or by use of diffractive optics that provide two foci. The result is one in-focus image and one out-of-focus image. The human brain disregards the out-of-focus image and concentrates on the in-focus image. The major disadvantage of this approach is that when an object is in between the ranges where one of the foci provides an in-focus image, the brain has difficulty in choosing which of the blurry images to pick. This causes headaches and difficulty in seeing. Another major disadvantage of this technique is that if the two images are not aligned (as occurs when the lens is not centered, a frequent occurrence with contact lenses) the images do not line up and the out-of-focus image is apparent. As such a two-foci contact lens moves, the images move with respect to each other. Another disadvantage is loss of contrast. That is, the image looks washed out. The loss of contrast is even worse when the object is located between a reading distance and a very long distance; examples include the distance to a computer screen, a television set, or music on a stand. In these cases, two poorly focused images are superimposed.

Another commonly used approach is called monovision: a person is fitted with a lens on one eye for reading, and another lens on the other eye for distance viewing. The brain then selects the best-focused image to concentrate on. Images of objects at an intermediate distance cannot be seen clearly. This approach works for many people, but the inability to fuse images that are not both focused has made this solution unusable for many others because the user sees two misregistered images. The human brain can adapt to unchanging visual conditions, even when they markedly affect the immediate visual perception. For example, the brain is able to adapt to two images, if one is in focus, by concentrating on the in-focus image and ignoring the other. Again, problems occur if neither image is in focus.

As another example, the human brain can accommodate for very large distortions present in varifocal lenses, which gradually move from providing clear vision at a distance, for objects seen through the upper portion of the lens, to providing clear vision of close objects when seen through the lower inside part of the lenses. Objects at an intermediate distance can be seen through the center of the lenses. In this case, there is no need for one of two images to be selected. The problem that some people have is getting used to the distortion.

There has been work that provides an in-focus image over a large range of object distances, but that work requires that the aperture diameter of the camera or lens be fixed.

Guang-ming Dai (in "Optical surface optimization for the correction of presbyopia," Applied Optics Vol. 45, No. 17, 10 Jun. 2006, p. 4184) teaches that pupil diameter is a factor in the performance of contact lenses and the like, and discusses designs that work well for different pupil sizes.

Many designs attempt to improve vision over a range of distances. For example, the Acuvue® Bifocal contact lens design includes five zones of alternating additive power, with the goal of near and distance focus zones present for various pupil sizes. The CooperVision Frequency® 55 +1.5D multifocal includes three zones of monotonically changing optical power (a central zone having constant power, a middle transition zone, and an outer zone with constant power). The design approach for these products is roughly even power distribution, with only rudimentary consideration of pupil effects. Modeling suggests that the performance of these two products is quite uneven over both distance and pupil size.

Prior work has been done in the area of extending depth of focus over range only. See for example U.S. Pat. No. 6,536,898, issued Mar. 25, 2003 by one of the present inventors (incorporated herein by reference). Also see "Extended depth of focus contact lenses for presbyopia," by A. Zlotnik et al., OPTICS LETTERS, Jul. 15, 2009, Vol. 34, No. 14, pp. 2219-2221.

There is a need to extend the depth of focus and, thus, the depth of field, of the human eye over both range and pupil diameter by modifying optical devices and optical elements including contact lenses, intraocular implants, eyeglasses, and/or the surface of the eye itself (with laser surgery, for example).

SUMMARY

An object of the present invention is to provide apparatus and techniques for extending the depth of focus of human eyes.

Apparatus and methods according to the present invention increase the depth of field and decrease chromatic aberration in human vision in order to correct for loss in refocusing ability and for chromatic aberration. Optics variations, such as changes in thickness or index of refraction of optical devices, contact lenses, intraocular implants, or the shape of the cornea or eye lens, affect the phase, or wavefront, of the light perceived by the eye. The optics variations are chosen such that the resulting point spread function remains relatively constant over a desired range of object distances and pupil diameters, and the modulation transfer function (MTF) has minimal changes with no nulls, or regions of loss of information. The optics variations provide a coded image on the retina. The human brain decodes this coded image, resulting in an in-focus image over the different pupil diameters and object distances. There are no annoying out-of-focus images in a scene because the images of objects at any distance provide images that are formed with essentially the same point-spread function. All images are seen as being in focus after the brain performs the necessary processing on this point-spread function that is the same for all distances of the extended depth of field.

The extended depth of field is generally accomplished by applying selected variations to these optical elements (e.g., by varying surface thickness of the cornea of the eye or the shape of a surface of a contact lens). These variations encode the wavefront to produce an extended depth of field (EDOF) and cause the optical transfer function to remain relatively constant within a large range of pupil diameters and a large range of distances from the in-focus position. The human brain undoes the extended-depth-of-field coding effects, resulting in an in-focus image over an increased depth of field. While the human brain cannot compensate for general out-of-focus images, where the amount of blur changes with distance from the in-focus plane and the type of blur changes with pupil diameter, it can compensate for the specific misfocus added by the optical wave modifier to do the extended-depth-of-field coding, because that misfocus causes little change in blur with distance or with pupil diameter, and the variations are selected so that little or no information is lost in the process. An indication of the loss of information is the presence of nulls in the modulation transfer function (MTF) of the imaging system. Images that are out of focus have nulls in the MTF, and hence lose some information. A lens that is properly encoded for an extended depth of field has no nulls in the MTF.

For cases where the person still has some refocusing capability, the eye will change focus such that the image of the object being viewed falls into the extended region where the brain can decode the image. In that case, less coding is required. In the case of an intraocular implant to replace a damaged lens, the amount of wavefront coding is tailored to give the required amount of invariance in the point-spread function. The depth of focus can be increased to be 800% or greater than that of a normal implant, largely independent of the pupil diameter.

The selected variations to be applied to a contact lens are typically symmetric phase distributions. This means that rotation, which is common in contact lenses, will cause no problem. Rotation would be no problem with implants or modification of the cornea, however, so asymmetric phase distributions could be used. The selected phase variation will modify the point spread function of the imaging system so that it does not change over a large distance or with large changes in the pupil diameter. There are a variety of wavefront coding shapes that can be used.

The out-of-focus EDOF Contact Lens has no zeros in the MTF—Hence the image has information content equivalent to the in-focus image (at lower SNR).

BRIEF DESCRIPTION OF THE DRAWINGS

FIGS. 7A-7C plot the MTF of a CooperVision Frequency® 55 center-distance lens, and FIGS. 7D-7F plot the MTFs of a CooperVision Frequency® 55 center-near lens. Note that a user wears one of each.

FIG. 8A is plot of the superposition of three point spread functions at 0, 1, and 2 diopters of an eye corrected with the EDOF optic of FIG. 12, given a pupil diameter of 2 mm. FIG. 8B is a superposition of three plots of point spread functions of an eye corrected with the EDOF optic of FIG. 12, given a pupil diameter of 3 mm. FIG. 8C is a superposition of three plots of point spread functions of an eye corrected with the EDOF optic of FIG. 12, given a pupil diameter of 4 mm. Note that the PSFs vary little with distance.

FIGS. 9A-9D are diagrams of optical devices with an EDOF coating applied to an optical element of each device. FIG. 9A is a side cutaway diagram of binoculars, FIG. 9B is a side view of the elements of a microscope, FIG. 9C is a side cutaway diagram of a prismatic telescope, and FIG. 9D is a side cutaway diagram of an astronomical telescope.

DETAILED DESCRIPTION OF THE PREFERRED EMBODIMENTS

Figure 1A:
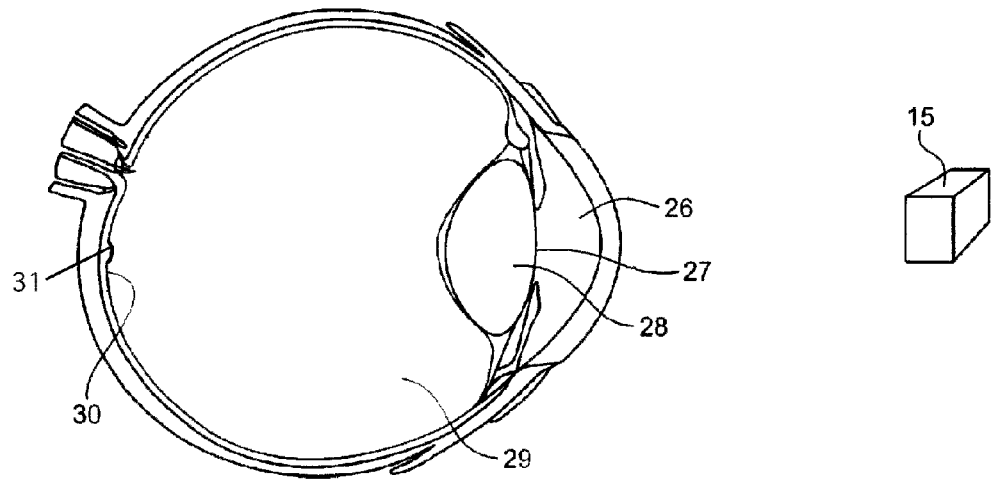
FIG. 1A (Prior Art) is a side cutaway view of a human eye with wrinkled retina.
Figure 1B:
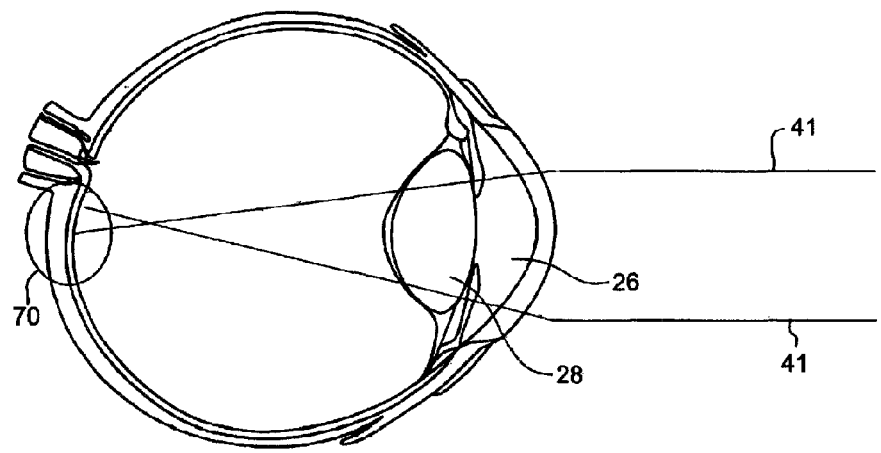
FIG. 1B (Prior Art) is a side cutaway view of a human eye having myopia.
Figure 1C:
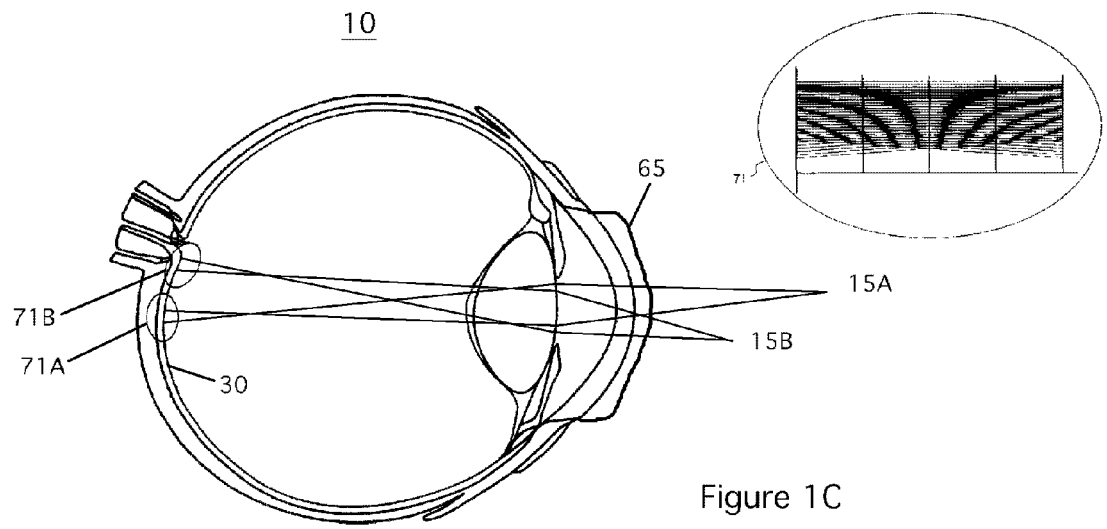
FIG. 1C is a side cutaway view of a human eye with a relatively small pupil diameter, with vision corrected by an extended depth of field (EDOF) contact lens according to the present invention. The profile of the micrometer-level profile in the EDOF contact lens is greatly exaggerated for clarity.

FIG. 1C is a side cutaway view of a human eye with a relatively small pupil diameter, with vision corrected by an extended depth of field (EDOF) contact lens 65 according to the present invention. The thickness and relative changes in thickness of lens 65 are greatly exaggerated for clarity. Light from a far object 15A and a near object 15B both have a slight misfocus 71A, 71B at retina 30. Unlike the misfocus in FIG. 1B (Prior Art), however, this misfocus causes little change in blur with distance, and the variations are selected so that little or no information is lost in the process. A person with wrinkled retina is able to see the entire image in focus, even the portion that is out of focus normally because that bit of the retina is out of place.

Figure 1D:
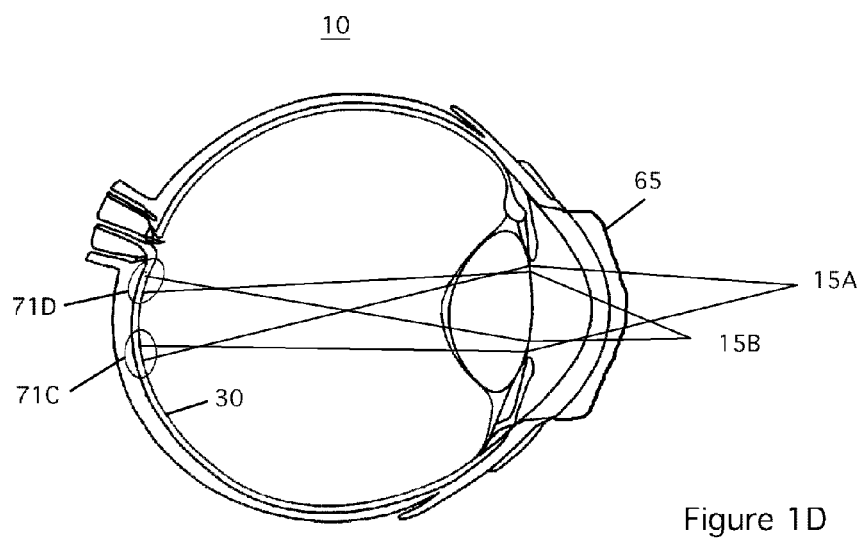
FIG. 1D is a side cutaway view of a human eye with a relatively large pupil diameter, with vision corrected by the extended depth of field (EDOF) contact lens of FIG. 1C.

FIG. 1D is a side cutaway view of a human eye with a relatively large pupil diameter, with vision corrected by an extended depth of field (EDOF) contact lens 65 according to the present invention. Again, light from a far object 15A and a near object 15B both have a slight misfocus 71C, 71D at retina 30. This misfocus causes little change in blur with distance, and in addition, little change in blur is seen compared with the results in FIG. 1C. Lens 65 has been chosen such that when light passes through a smaller portion of the lens (because the pupil diameter is smaller) it has similar misfocus as when light passes through a larger portion of the lens. Again the variations are chosen so that little information is lost due to the lens.

Figure 2:
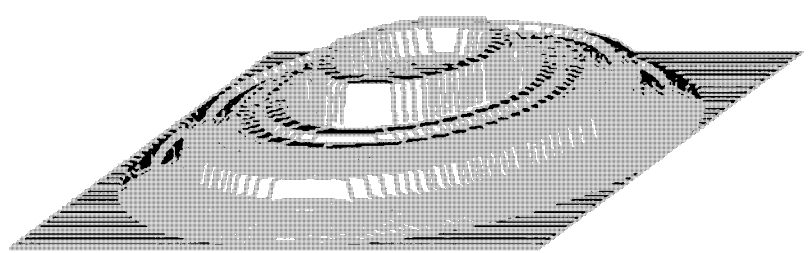
FIG. 2 is an isometric plot showing the profile of an example contact lens according to the present invention.

FIG. 2 is an isometric view of a first embodiment of an extended depth of field (EDOF) contact lens 65 according to the present invention. The profile of lens 65 comprises concentric, circularly symmetric rings of varying depth. The structure of the lens is chosen such that the optical transfer function remains relatively constant over a range of pupil diameters, as well as object distances. The circularly symmetric structure is advantageous in that a user does not have to worry about contact lenses rotating. It also simplifies manufacturing.

Figure 3:
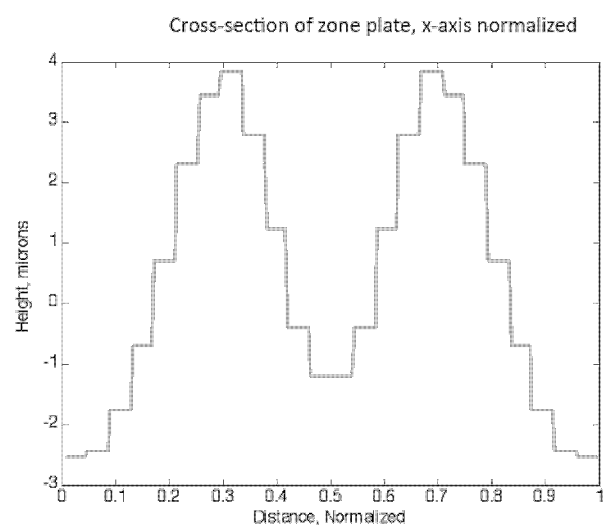
FIG. 3 is a 2-Dimensional plot showing the profile of an example contact lens according to the present invention.

FIG. 3 is a plot showing the profile of a second embodiment of an EDOF optic according to the present invention. The x-axis has been normalized. In general, a contact lens will have a diameter on the order of 6 mm.

Figure 4:
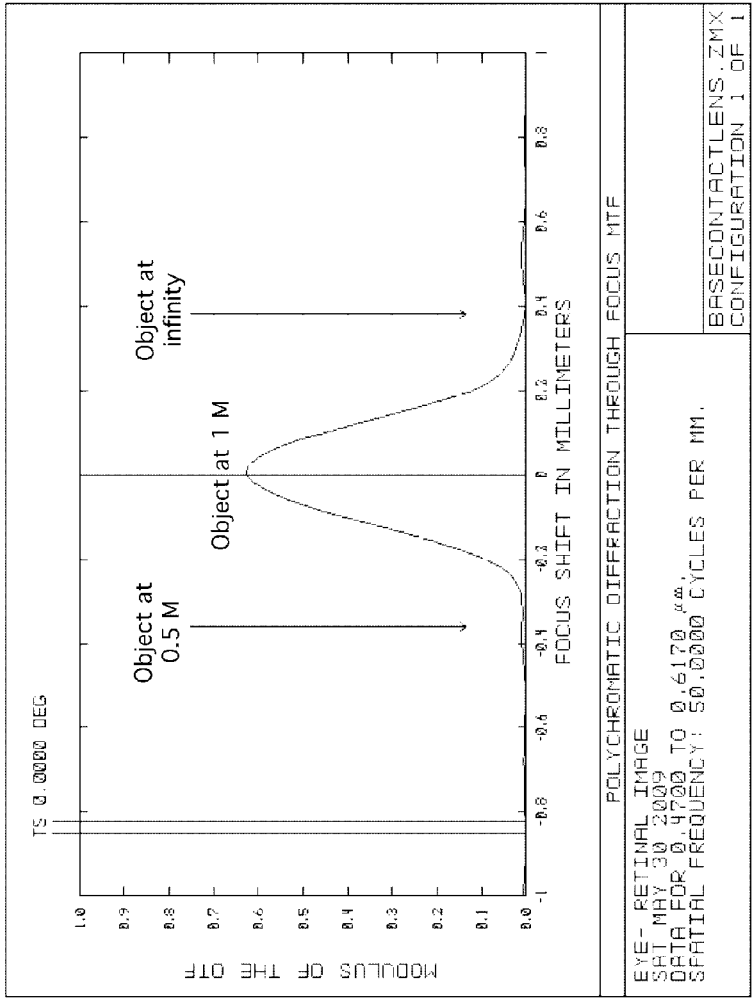
FIG. 4 is a plot showing a through-focus modulation transfer function for a 50 line pair/mm object of a normal human eye focusing on an object one meter away.

FIG. 4 is a plot showing a modulation transfer function of a normal human eye focusing on an object one meter away. The human eye focuses by changing the shape of its lens 28 (see FIG. 1, Prior Art). The x-axis of the plot of FIG. 4 is the focus shift away from the ideal focus of lens 28. The focus shift of the eye in order to focus at infinity is shown (1 diopter, or approximately 0.38 mm) and the focus shift to focus at 0.5 mm is also shown (1 diopter, or approximately −0.36 mm). Objects can't be further away than infinity, but the eye can shift focus past the equivalent focus shift, so the plot extends further than where "object at infinity" is indicated. Note that the MTF is far from uniform, and includes zeroes, albeit outside the relevant focus shift range. The peak of the MTF is over 6, and the minimum in the relevant range is near zero.

Figure 5:
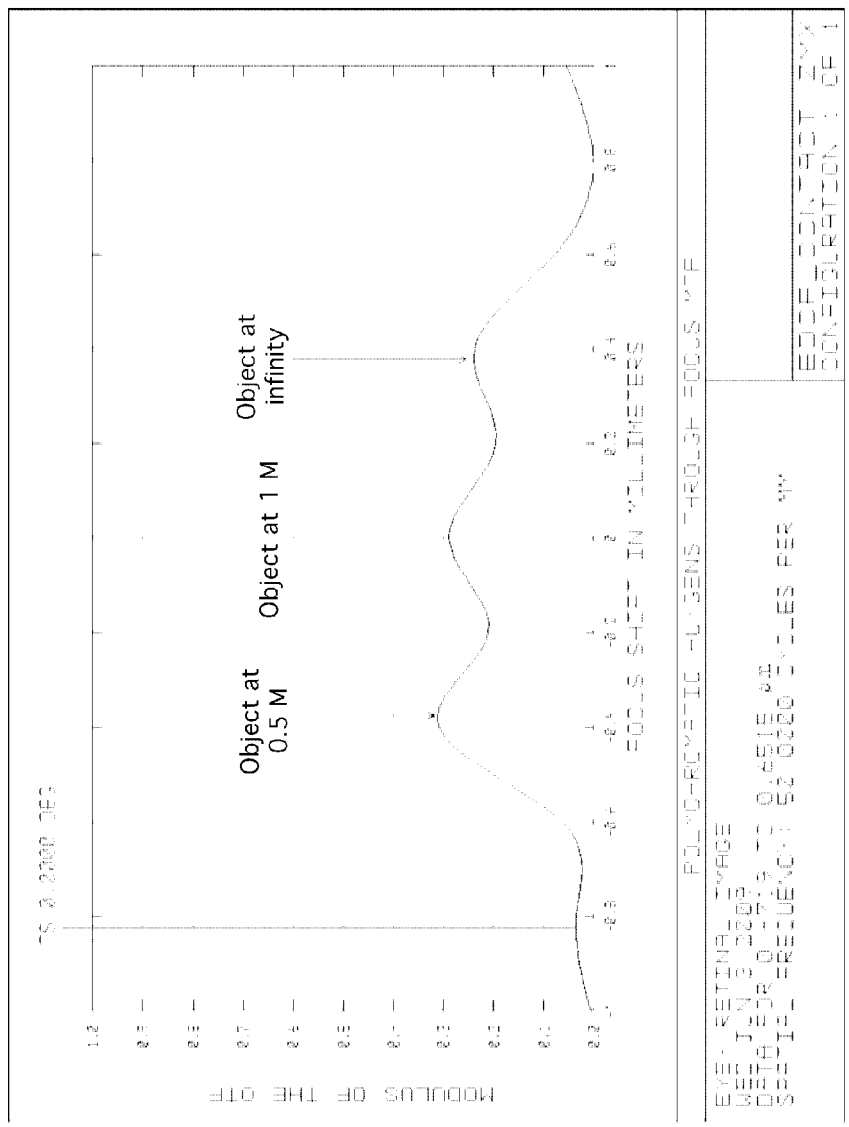
FIG. 5 is a plot showing a through-focus contrast modulation transfer function at 50 line pairs per mm of an eye with vision corrected by an EDOF optic such as the contact lens of FIGS. 2 and 3.

FIG. 5 is a plot showing a through-focus contrast modulation transfer function, at 50 line pairs per mm in the image, of an eye with vision corrected by an EDOF optic for comparison with the equivalent plot for the normal lens without EDOF shown in FIG. 4. In FIG. 5, the MTF is much more uniform over the relevant focus shift range, and does not include zeroes until well past the range. The peak is about 0.31, and the minimum is about 0.19. Thus, the minimum is over half of the maximum. In fact that variation from the maximum is under 40%. Similar results are seen when comparing MTFs at different pupil diameters. The MTF FWHM at the same focus shift is generally within about ⅓ of the maximum, for pupil diameters ranging from 2-4 mm. For pupil diameters ranging from 2-3 mm, the MTF widths are even closer—usually within 50% of the maximum or less.

Figure 6A:
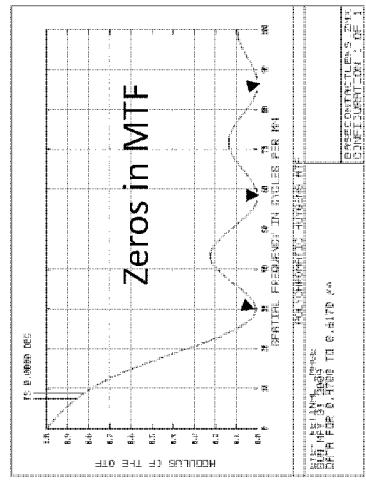
FIG. 6A is a plot showing a modulation transfer function of a normal human eye in focus.
Figure 6B:
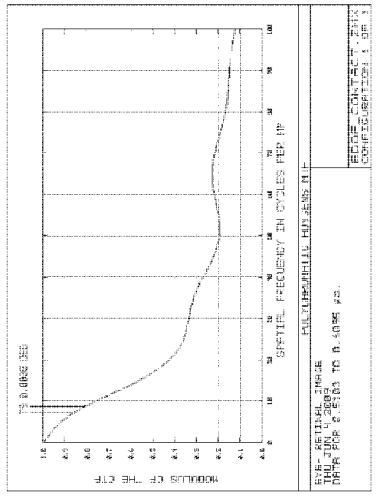
FIG. 6B is a plot showing a modulation transfer function of a normal human eye out of focus. The loss of information caused by the zeros in the MTF is clearly seen.
Figure 6C:
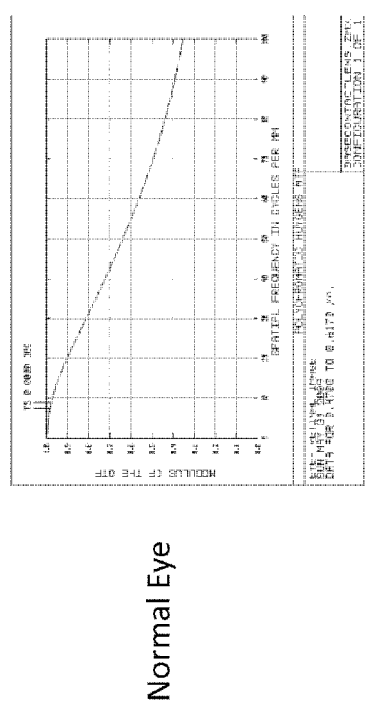
FIG. 6C is a plot showing a modulation transfer function of an eye with vision corrected by an EDOF optic such as the contact lens of FIG. 2, in focus.
Figure 6D:
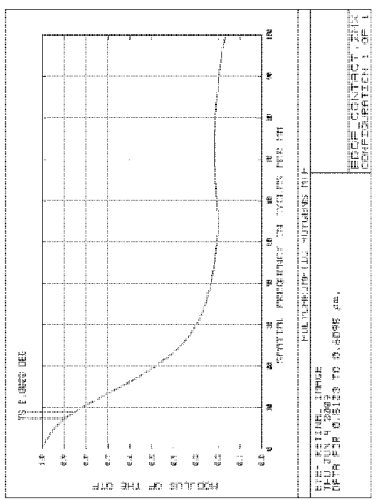
FIG. 6D is a plot showing a modulation transfer function of an eye with vision corrected by an EDOF optic such as the contact lens of FIG. 3, out of focus by one diopter.

FIGS. 6A-6D plot MTF versus spatial frequency (0-100 cycles/mm). FIG. 6A is a plot showing a modulation transfer function of a normal human eye in focus. FIG. 6B is a plot showing a modulation transfer function of a normal human eye out of focus. Because the out-of-focus MTF has zeros in the Modulation Transfer Function, information is irretrievably lost. FIG. 6C is a plot showing a modulation transfer function of an eye with vision corrected by an EDOF contact lens, in focus. FIG. 6D is a plot showing a modulation transfer function of an eye with vision corrected by an EDOF contact lens according to the present invention, out of focus. The out-of-focus EDOF Contact Lens has no zeros in the MTF—Hence the image has information content equivalent to the in-focus image (at lower SNR). The ideal image can be recovered from a wave front coded (WFC) image with a linear filtering operation (deconvolution) on the image. There is evidence that the Human visual system learns image processing tasks equivalent to the deconvolution required for recovering the contrast in a WFC image.

FIGS. 7A-7I are plots showing the MTFs of prior art devices versus focus shift at various pupil diameters. These plots are comparable to those shown in FIGS. 4 and 5. The higher maximum MTF in each case is for a 25 lp/mm object, and the lower maximum MTF is for a 50 lp/mm object.

Figure 7A:
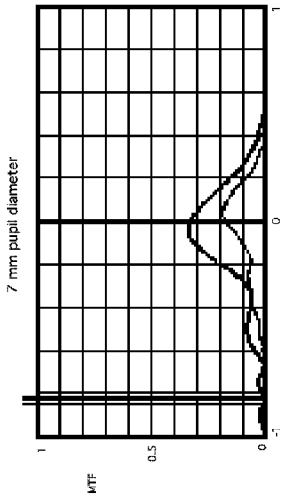
FIGS. 7A-7I are plots showing the MTFs of prior art devices versus focus shift at various pupil diameters. These plots are comparable to those shown in FIGS. 4 and 5.
Figure 7B:
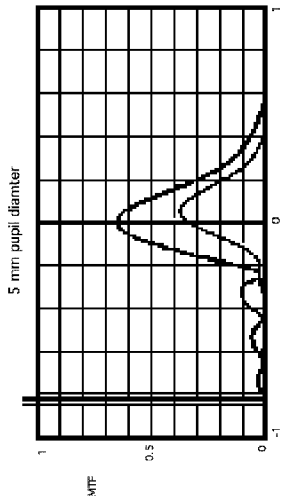
Figure 7C:
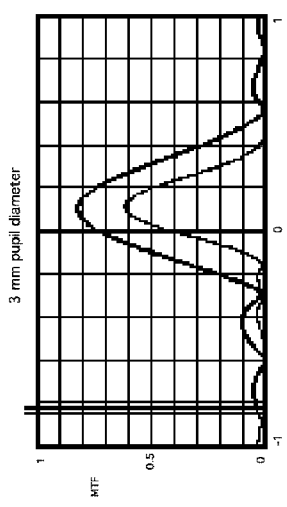
Figure 7D:
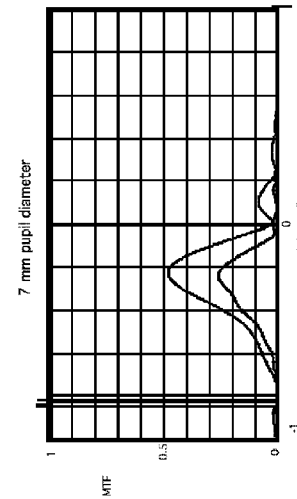
Figure 7E:
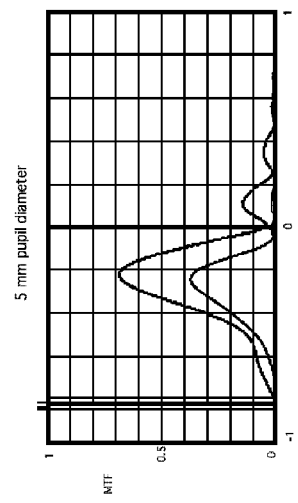
Figure 7F:
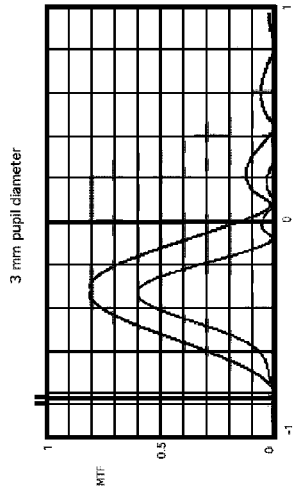

FIGS. 7A-7C plot the MTF of a CooperVision Frequency® 55 center-distance lens, and FIGS. 7D-7F plot the MTFs of a CooperVision Frequency® 55 center-near lens. Note that a user wears one of each. The MTFs are far from uniform, and have zeroes in the relevant ranges. This indicates that the user's vision is varies substantially over distance, which is in fact the case.

Figure 7I:
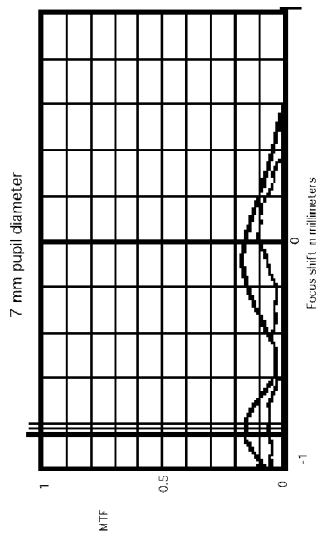
Figure 7H:
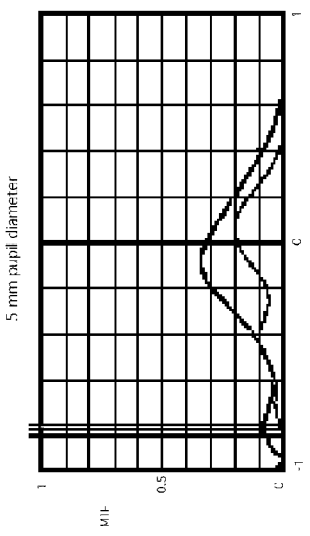
Figure 7G:
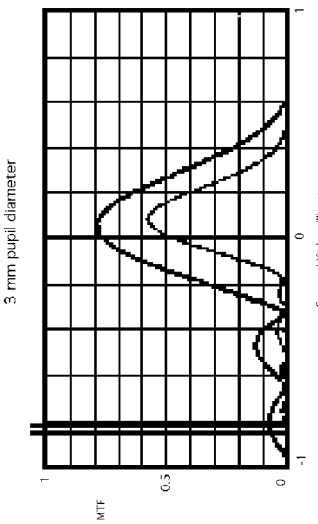

FIGS. 7G-7I plot the MTF of an Acuvue® Bifocal +1D lens. Again, the MTF are far from uniform and include zeroes.

Figure 8A:
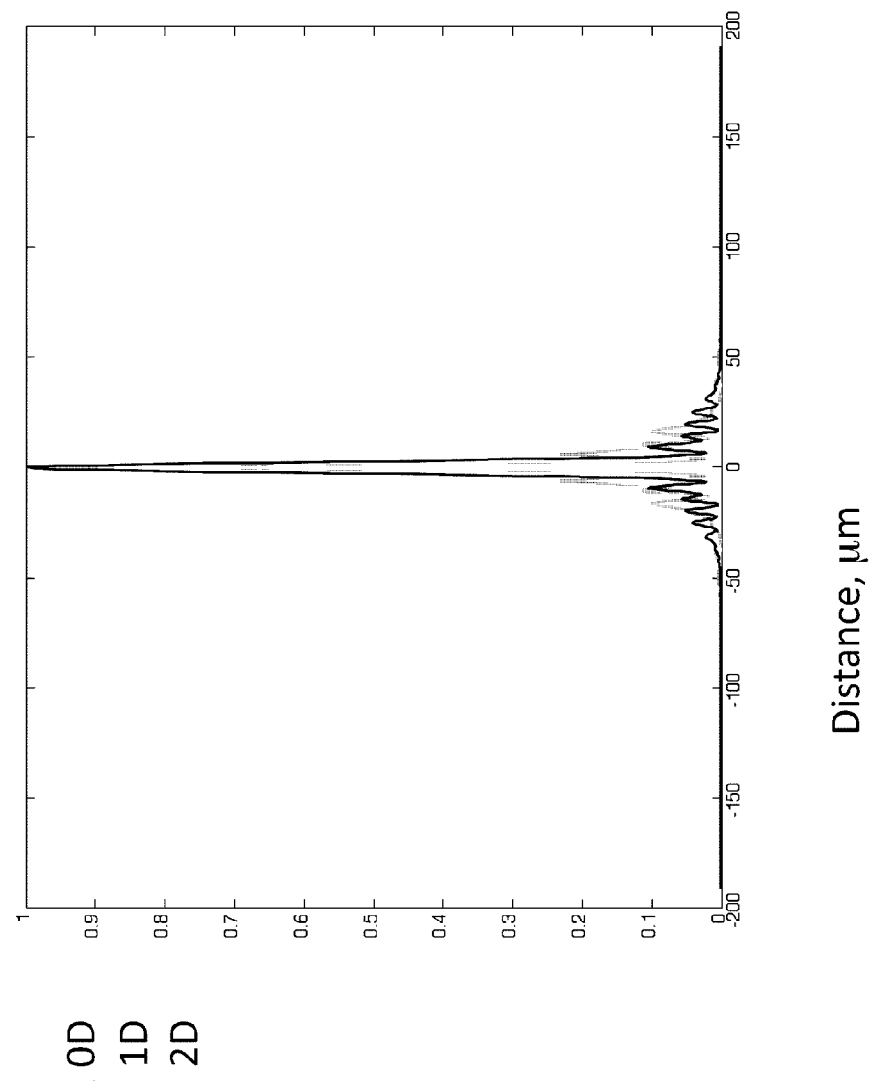
FIGS. 8A-8C are two-dimensional plots of point spread functions (PDF) of an eye with vision corrected by an EDOF optic such as the contact lens of FIG. 3, given pupil diameters of 2-4 mm.
Figure 8B:
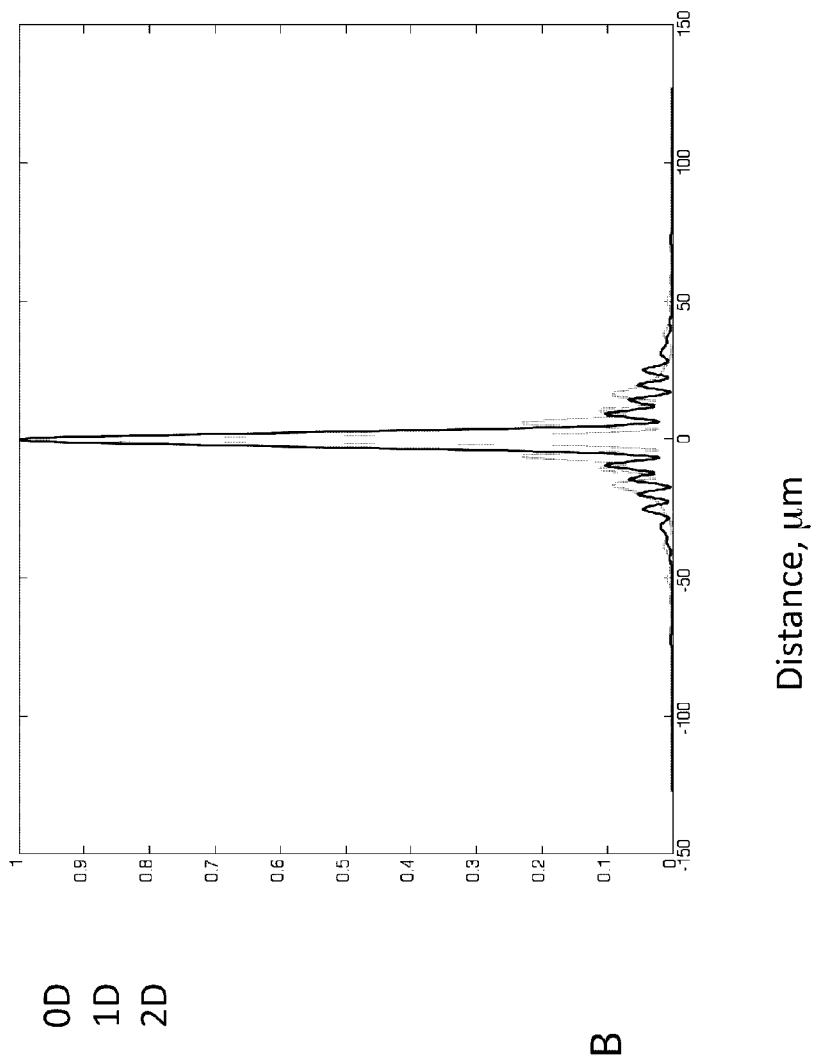
Figure 8C:
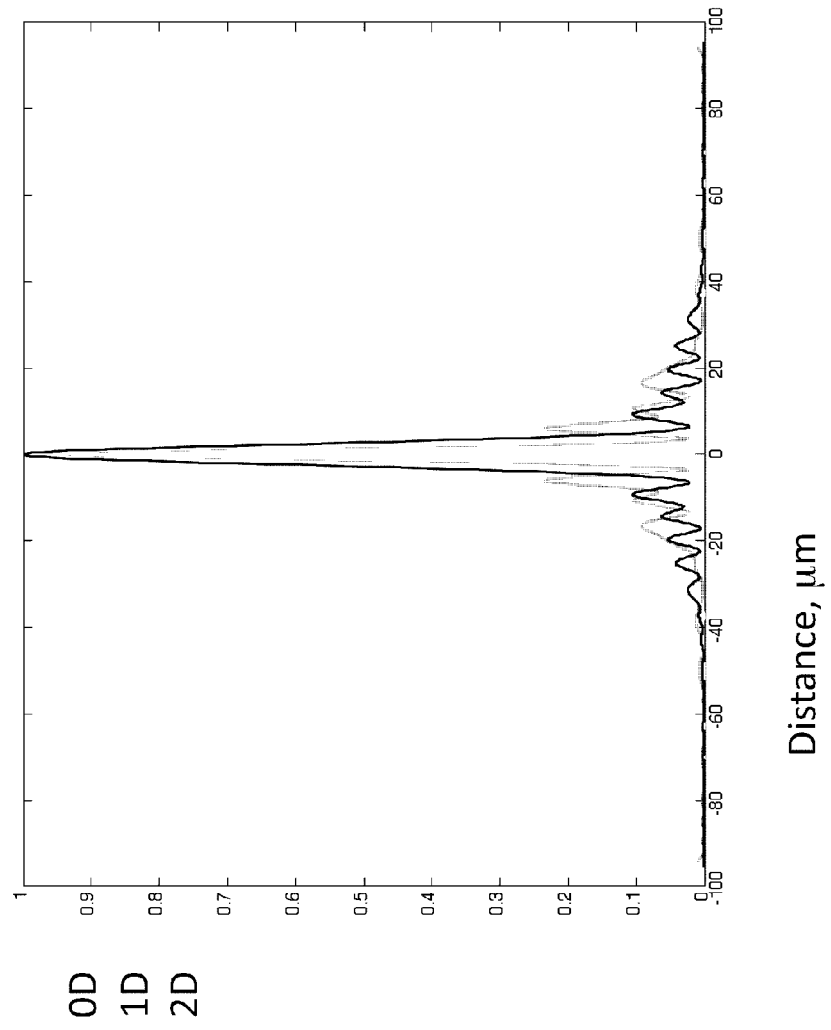

FIGS. 8A-8C are plots of point spread function (PSF) for varying pupil diameters. Each figure includes PSF plots for 0, 1, and 2 diopters (roughly equivalent to an object at infinity, 1 M and 0.5 M). The plots are normalized to have the maximum value for each curve at 1. Thus each figure shows the variation in normalized PSF over distance for a given pupil diameter, and the three figures together show the variation in PSF over pupil diameter.

FIG. 8A is plot of PSFs of an eye corrected with the EDOF optic of FIG. 3, given a pupil diameter of 2 mm. The three point spread functions are sampled at 0, 1, and 2 diopters. Note that the point spread function plots are very similar, though the higher diopter plots are slightly wider. The full width at half maximum (FWHM) values are well within 20% of each other.

FIG. 8B is plot of PSFs of an eye corrected with the EDOF optic of FIG. 3, given a pupil diameter of 3 mm. The three point spread functions are sampled at 0, 1, and 2 diopters. The FWHMs are again well within 20% of the maximum.

FIG. 8C is plot of PSFs of an eye corrected with the EDOF optic of FIG. 3, given a pupil diameter of 4 mm. The three point spread functions are sampled at 0, 1, and 2 diopters. The FWHMs are well within 20% of the maximum. Comparing the PSFs over pupil diameters, the PSFs vary more, but the narrowest FWHMs are still generally at least about 30% of the maximum FWHMs, and minimum FWHMs for 2 mm and 3mm are within 50% of the maximum.

FIGS. 9A-9D are diagrams of optical devices with an EDOF coating applied to an optical element of each device. FIG. 9A is a side cutaway diagram of binoculars, FIG. 9B is a side view of the elements of a microscope, FIG. 9C is a side cutaway diagram of a prismatic telescope, and FIG. 9D is a side cutaway diagram of an astronomical telescope. An EDOF surface according to the present invention could be applied to any of the lenses 20. In addition, EDOF surface could be applied to the mirrors in an optical system. In each case, the PSFs should be similar over distance and pupil diameter, and the MTFs should be relatively uniform and not contain zeroes.

It will be appreciated by one skilled in the art that there are many possible variations on these designs that fall within the scope of the present invention.

What is claimed is:

1. Apparatus for increasing the depth of field of human vision comprising:
   an optical element positioned between objects to be viewed and a retina of an eye, the element being constructed and arranged to alter the phase of light at the retina such that—
      the modulation transfer function (MTF) of imaged objects at the retina is relatively uniform over pupil diameter compared to the modulation transfer function without the element; and
      the MTF is relatively uniform over object distance compared to the modulation transfer function without the element; and
      the MTF does not contain zeroes.

2. The apparatus of claim 1 wherein the element comprises one of the following:
   a contact lens;
   an intraocular implant;
   a surface of the eye;
   an optical element within a telescope;
   an optical element within a microscope
   an optical element within binoculars.

3. The apparatus of claim 1 wherein the minimum MTF of an imaged object at the retina over a pupil diameter range from 2 mm to 4 mm is at least 50% of the maximum MTF.

4. The apparatus of claim 3 wherein the element comprises one of the following:
   a contact lens;
   an intraocular implant;
   a surface of the eye;
   an optical element within a telescope;
   an optical element within a microscope
   an optical element within binoculars.

5. The apparatus of claim 3 wherein the minimum MTF over an object distance range from 0.5 meters to infinity is at least 50% of the maximum MTF.

6. The apparatus of claim 3 wherein the difference between full widths at half maximum (FWHMs) of point spread functions (PSFs) of imaged objects at the retina is substantially less than the difference between FWHMs of PSFs of imaged objects at the retina without the element.

7. The apparatus of claim 6 wherein the narrowest FWHM of PSFs of imaged objects at the retina is at 30% of largest FWHM over a pupil diameter range of 2 mm to 4 mm.

8. The apparatus of claim 7 wherein the narrowest FWHM of PSFs of imaged objects at the retina is at 80% of largest FWHM over an object distance range from 0.5 meters to infinity.

9. The method of manufacturing apparatus for improving depth of field of human vision comprising the following steps:
   (a) selecting an optical system for use with human vision; and
   (b) fabricating an optical element within the selected system such that the MTF of imaged objects at a retina using the selected system is relatively uniform over pupil diameter and object distance compared to the MTF without the system.

10. The method of claim 9 wherein step (a) selects from among the following:
   a contact lens;
   an intraocular implant;
   a surface of the eye;
   an optical element within a telescope;
   an optical element within a microscope
   an optical element within binoculars.

11. The method of claim 9 wherein the optical element is fabricated such that minimum MTF of an imaged object at the retina over a pupil diameter range from 2 mm to 4 mm is at least 50% of the maximum MTF.

* * * * *